United States Patent
Raymond et al.

(10) Patent No.: US 11,083,904 B2
(45) Date of Patent: Aug. 10, 2021

(54) BISPHASIC OR MULTIPHASIC PULSE WAVEFORM AND METHOD

(71) Applicant: CardioThrive, Inc., Concord, CA (US)

(72) Inventors: Douglas M. Raymond, Livermore, CA (US); Peter D. Gray, Vallejo, CA (US); Walter T. Savage, Concord, CA (US); Shelley J. Savage, Concord, CA (US)

(73) Assignee: CARDIOTHRIVE, INC., Concord, CA (US)

( * ) Notice: Subject to any disclaimer, the term of this patent is extended or adjusted under 35 U.S.C. 154(b) by 0 days.

(21) Appl. No.: 15/894,685

(22) Filed: Feb. 12, 2018

(65) Prior Publication Data

US 2018/0161584 A1 Jun. 14, 2018

Related U.S. Application Data

(63) Continuation of application No. 15/811,427, filed on Nov. 13, 2017, now Pat. No. 10,870,012, which is a continuation of application No. 14/662,137, filed on Mar. 18, 2015, now Pat. No. 9,833,630, which is a continuation-in-part of application No. 14/303,541, filed on Jun. 12, 2014, now Pat. No. 9,616,243.

(60) Provisional application No. 61/835,443, filed on Jun. 14, 2013.

(51) Int. Cl.
*A61N 1/39* (2006.01)
*A61N 1/362* (2006.01)

(52) U.S. Cl.
CPC ......... *A61N 1/3906* (2013.01); *A61N 1/3912* (2013.01); *A61N 1/3625* (2013.01)

(58) Field of Classification Search
CPC ... A61N 1/3906; A61N 1/3912; A61N 1/3625
USPC ....................................................... 607/5, 59
See application file for complete search history.

(56) References Cited

U.S. PATENT DOCUMENTS

| | | | |
|---|---|---|---|
| 3,782,389 A | 1/1974 | Bell | |
| 4,328,808 A | 5/1982 | Charbonnier et al. | |
| 4,441,498 A | 4/1984 | Nordling | |
| 4,957,109 A | 9/1990 | Groeger et al. | |
| 5,199,429 A | 4/1993 | Kroll et al. | |
| 5,240,995 A | 8/1993 | Gyory | |
| 5,290,585 A | 3/1994 | Elton | |

(Continued)

FOREIGN PATENT DOCUMENTS

| | | |
|---|---|---|
| CN | 101201277 A | 6/2008 |
| CN | 101919682 A | 12/2010 |

(Continued)

OTHER PUBLICATIONS

"Changes in the passive electrical properties of human stratum corneum due electroporation" dated Dec. 7, 1994. By U. Pliquett, R. Langer, and J. C. Weaver (11 pages).

(Continued)

*Primary Examiner* — Amanda K Hulbert
*Assistant Examiner* — Philip C Edwards
(74) *Attorney, Agent, or Firm* — DLA Piper LLP (US)

(57) ABSTRACT

A novel therapeutic biphasic or multiphasic pulse waveform and method are provided. The novel therapeutic biphasic or multiphasic pulse waveform may be used in a defibrillator, or in another medical device that delivers therapeutic electrical stimulation pulses to a patient.

5 Claims, 13 Drawing Sheets

(56) References Cited

U.S. PATENT DOCUMENTS

| | | |
|---|---|---|
| 5,338,490 A | 8/1994 | Dietz |
| 5,341,806 A | 8/1994 | Gadsby et al. |
| 5,362,420 A | 11/1994 | Itoh |
| 5,369,351 A | 11/1994 | Adams |
| 5,391,186 A | 2/1995 | Kroll et al. |
| 5,402,884 A | 4/1995 | Gilman et al. |
| 5,489,624 A | 2/1996 | Kantner |
| 5,507,781 A | 4/1996 | Kroll et al. |
| 5,536,768 A | 7/1996 | Kantner |
| 5,573,668 A | 11/1996 | Grosh |
| 5,620,464 A | 4/1997 | Kroll et al. |
| 5,643,252 A | 7/1997 | Waner et al. |
| 5,658,316 A | 8/1997 | Lamond et al. |
| 5,660,178 A | 8/1997 | Kantner |
| 5,733,310 A | 3/1998 | Lopin et al. |
| 5,800,685 A | 9/1998 | Perrault |
| 5,871,505 A | 2/1999 | Adams |
| 5,919,220 A | 7/1999 | Stieglitz et al. |
| 5,987,354 A | 11/1999 | Cooper |
| 6,004,312 A | 12/1999 | Finneran et al. |
| 6,006,131 A | 12/1999 | Cooper et al. |
| 6,056,738 A | 5/2000 | Marchitto et al. |
| 6,115,623 A | 9/2000 | McFee et al. |
| 6,141,584 A | 10/2000 | Rockwell et al. |
| 6,169,923 B1 | 1/2001 | Kroll et al. |
| 6,173,198 B1 | 1/2001 | Schulze et al. |
| 6,197,324 B1 | 3/2001 | Crittenden |
| 6,251,100 B1 | 6/2001 | Flock et al. |
| 6,256,533 B1 | 7/2001 | Yuzhakov et al. |
| 6,266,563 B1 | 7/2001 | Kenknight et al. |
| 6,315,722 B1 | 11/2001 | Yaegashi |
| 6,329,488 B1 | 12/2001 | Terry |
| 6,379,324 B1 | 4/2002 | Gartstein et al. |
| 6,477,413 B1 | 11/2002 | Sullivan et al. |
| 6,576,712 B2 | 6/2003 | Feldstein |
| 6,596,401 B1 | 7/2003 | Terry |
| 6,597,948 B1 | 7/2003 | Rockwell et al. |
| 6,611,707 B1 | 8/2003 | Prausnitz |
| 6,690,959 B2 | 2/2004 | Thompson |
| 6,714,817 B2 | 3/2004 | Daynes et al. |
| 6,714,824 B1 | 3/2004 | Ohta et al. |
| 6,797,276 B1 | 9/2004 | Glenn |
| 6,803,420 B2 | 10/2004 | Cleary |
| 6,908,453 B2 | 6/2005 | Fleming |
| 6,908,681 B2 | 6/2005 | Terry |
| 6,931,277 B1 | 8/2005 | Yuzhakov |
| 7,069,075 B2 | 6/2006 | Olson |
| 7,072,712 B2 | 7/2006 | Kroll et al. |
| 7,108,681 B2 | 9/2006 | Gartstein |
| 7,215,991 B2 | 5/2007 | Besson et al. |
| 7,226,439 B2 | 6/2007 | Pransnitz |
| 7,463,917 B2 | 12/2008 | Martinez |
| 7,645,263 B2 | 1/2010 | Angel et al. |
| 7,797,044 B2 | 9/2010 | Covey et al. |
| 7,844,316 B1 | 11/2010 | Botero |
| 8,019,402 B1 | 9/2011 | Kryzpow et al. |
| 8,024,037 B2 | 9/2011 | Kumar et al. |
| 8,095,206 B2 | 1/2012 | Ghanem et al. |
| 8,295,902 B2 | 10/2012 | Salahieh et al. |
| 8,333,239 B2 | 12/2012 | Schneider et al. |
| 8,527,044 B2 | 9/2013 | Edwards et al. |
| 8,558,499 B2 | 10/2013 | Ozaki et al. |
| 8,615,295 B2 | 12/2013 | Savage et al. |
| 8,781,576 B2 | 7/2014 | Savage et al. |
| 8,938,303 B1 | 1/2015 | Matsen |
| 9,089,718 B2 | 7/2015 | Owen et al. |
| 9,101,778 B2 | 8/2015 | Savage et al. |
| 9,174,061 B2 | 11/2015 | Freeman et al. |
| 9,289,620 B2 | 3/2016 | Efimov et al. |
| 9,616,243 B2 | 4/2017 | Raymond et al. |
| 9,656,094 B2 | 5/2017 | Raymond et al. |
| 9,855,440 B2 | 1/2018 | Raymond et al. |
| 9,907,970 B2 | 3/2018 | Raymond et al. |
| 10,149,973 B2 | 12/2018 | Raymond et al. |
| 10,279,189 B2 | 5/2019 | Raymond et al. |
| 10,828,500 B2 | 11/2020 | Savage et al. |
| 2001/0027270 A1 | 10/2001 | Stratbucker |
| 2001/0031992 A1 | 10/2001 | Fishier et al. |
| 2001/0034487 A1 | 10/2001 | Cao et al. |
| 2001/0051819 A1 | 12/2001 | Fishier et al. |
| 2002/0016562 A1 | 2/2002 | Cormier et al. |
| 2002/0045907 A1 | 4/2002 | Sherman et al. |
| 2002/0082644 A1 | 6/2002 | Picardo et al. |
| 2003/0017743 A1 | 1/2003 | Picardo et al. |
| 2003/0055460 A1 | 3/2003 | Owen et al. |
| 2003/0088279 A1 | 5/2003 | Rissmann et al. |
| 2003/0125771 A1 | 7/2003 | Garrett et al. |
| 2003/0163166 A1 | 8/2003 | Sweeney et al. |
| 2003/0167075 A1 | 9/2003 | Fincke |
| 2003/0197487 A1 | 10/2003 | Tamura et al. |
| 2004/0105834 A1 | 6/2004 | Singh |
| 2004/0143297 A1 | 7/2004 | Maynard |
| 2004/0166147 A1 | 8/2004 | Lundy |
| 2004/0225210 A1 | 11/2004 | Brosovich et al. |
| 2004/0247655 A1 | 12/2004 | Asmus |
| 2005/0055460 A1 | 3/2005 | Johnson et al. |
| 2005/0107713 A1 | 5/2005 | Van Herk |
| 2005/0107833 A1 | 5/2005 | Freeman et al. |
| 2005/0123565 A1 | 6/2005 | Subramony |
| 2005/0246002 A1 | 11/2005 | Martinez |
| 2006/0136000 A1 | 6/2006 | Bowers |
| 2006/0142806 A1 | 6/2006 | Katzman et al. |
| 2006/0173493 A1 | 8/2006 | Armstrong et al. |
| 2006/0206152 A1 | 9/2006 | Covey et al. |
| 2007/0016268 A1 | 1/2007 | Carter et al. |
| 2007/0078376 A1 | 4/2007 | Smith |
| 2007/0135729 A1 | 6/2007 | Ollmar et al. |
| 2007/0143297 A1 | 6/2007 | Recio et al. |
| 2007/0150008 A1 | 6/2007 | Jones et al. |
| 2007/0191901 A1 | 8/2007 | Schecter |
| 2008/0082153 A1 | 4/2008 | Gadsby et al. |
| 2008/0097546 A1 | 4/2008 | Powers et al. |
| 2008/0114232 A1 | 5/2008 | Gazit |
| 2008/0154110 A1 | 6/2008 | Burnes et al. |
| 2008/0154178 A1 | 6/2008 | Carter et al. |
| 2008/0177342 A1 | 7/2008 | Snyder |
| 2008/0200973 A1 | 8/2008 | Mallozzi et al. |
| 2008/0312579 A1 | 12/2008 | Chang et al. |
| 2008/0312709 A1 | 12/2008 | Volpe et al. |
| 2009/0005827 A1 | 1/2009 | Weintraub et al. |
| 2009/0024189 A1* | 1/2009 | Lee ............ A61N 1/36017 607/66 |
| 2009/0076366 A1 | 3/2009 | Palti |
| 2009/0210022 A1 | 8/2009 | Powers |
| 2009/0318988 A1 | 12/2009 | Powers |
| 2009/0326400 A1 | 12/2009 | Huldt |
| 2010/0030290 A1* | 2/2010 | Bonner ............ A61N 1/385 607/5 |
| 2010/0036230 A1 | 2/2010 | Greene et al. |
| 2010/0063559 A1 | 3/2010 | McIntyre et al. |
| 2010/0160712 A1 | 6/2010 | Burnett et al. |
| 2010/0181069 A1 | 7/2010 | Schneider et al. |
| 2010/0191141 A1 | 7/2010 | Aberg |
| 2010/0241181 A1 | 9/2010 | Savage et al. |
| 2010/0249860 A1 | 9/2010 | Shuros et al. |
| 2011/0028859 A1 | 2/2011 | Chian |
| 2011/0071611 A1 | 3/2011 | Khuon et al. |
| 2011/0208029 A1 | 8/2011 | Joucla et al. |
| 2011/0237922 A1 | 9/2011 | Parker, III et al. |
| 2011/0288604 A1 | 11/2011 | Kaib et al. |
| 2011/0301683 A1 | 12/2011 | Axelgaard |
| 2012/0101396 A1 | 4/2012 | Solosko et al. |
| 2012/0112903 A1 | 5/2012 | Kalb et al. |
| 2012/0136233 A1 | 5/2012 | Yamashita |
| 2012/0158075 A1 | 6/2012 | Kaib et al. |
| 2012/0158078 A1 | 6/2012 | Moulder et al. |
| 2012/0203079 A1 | 8/2012 | McLaughlin |
| 2012/0203297 A1 | 8/2012 | Efimov et al. |
| 2012/0259382 A1 | 10/2012 | Trier |
| 2013/0018251 A1 | 1/2013 | Caprio et al. |
| 2013/0144365 A1 | 6/2013 | Kipke et al. |
| 2014/0005736 A1 | 1/2014 | Badower |
| 2014/0039593 A1 | 2/2014 | Savage et al. |
| 2014/0039594 A1 | 2/2014 | Savage et al. |

(56) References Cited

U.S. PATENT DOCUMENTS

| | | |
|---|---|---|
| 2014/0221766 A1 | 8/2014 | Kinast |
| 2014/0276183 A1 | 9/2014 | Badower |
| 2014/0277226 A1 | 9/2014 | Poore et al. |
| 2014/0317914 A1 | 10/2014 | Shaker |
| 2014/0324113 A1 | 10/2014 | Savage et al. |
| 2014/0371566 A1 | 12/2014 | Raymond et al. |
| 2014/0371567 A1 | 12/2014 | Raymond et al. |
| 2014/0371805 A1 | 12/2014 | Raymond et al. |
| 2014/0371806 A1 | 12/2014 | Raymond et al. |
| 2015/0297104 A1 | 10/2015 | Chen et al. |
| 2015/0327781 A1 | 11/2015 | Hernandez-Silveira |
| 2016/0206893 A1 | 7/2016 | Raymond et al. |
| 2016/0213933 A1 | 7/2016 | Raymond et al. |
| 2016/0213938 A1 | 7/2016 | Raymond et al. |
| 2016/0296177 A1 | 10/2016 | Gray et al. |
| 2016/0361533 A1 | 12/2016 | Savage et al. |
| 2016/0361555 A1 | 12/2016 | Savage et al. |
| 2017/0108447 A1 | 4/2017 | Lin |
| 2017/0252572 A1 | 9/2017 | Raymond et al. |
| 2018/0064948 A1 | 3/2018 | Raymond et al. |
| 2018/0117347 A1 | 5/2018 | Raymond et al. |
| 2018/0200528 A1 | 7/2018 | Savage et al. |
| 2019/0175898 A1 | 6/2019 | Raymond et al. |
| 2019/0192867 A1 | 6/2019 | Savage et al. |
| 2019/0321650 A1 | 10/2019 | Raymond et al. |
| 2020/0406045 A1 | 12/2020 | Raymond et al. |

FOREIGN PATENT DOCUMENTS

| | | |
|---|---|---|
| DE | 10 2006 025864 | 12/2007 |
| EP | 1 530 983 | 5/2005 |
| EP | 1 834 622 | 9/2007 |
| EP | 2442867 A1 | 4/2012 |
| GB | 2085593 | 4/1982 |
| JP | 2000-093526 | 1/1917 |
| JP | 2011-512227 | 9/1917 |
| JP | 2012-501789 | 9/1917 |
| JP | S63-296771 | 9/1917 |
| JP | 2001506157 A | 5/2001 |
| JP | 2005-144164 | 6/2005 |
| JP | 2006507096 A | 3/2006 |
| JP | 2007-530124 | 11/2007 |
| JP | 2008-302254 | 12/2008 |
| JP | 2010-511438 | 4/2010 |
| JP | 2010-529897 | 9/2010 |
| JP | 2011177590 A | 9/2011 |
| JP | 2012-135457 | 7/2012 |
| JP | 2012-529954 | 11/2012 |
| JP | 2013525084 A | 6/2013 |
| MX | 2010000638 A | 7/2010 |
| WO | WO9826841 A1 | 6/1998 |
| WO | WO 2003/020362 | 3/2003 |
| WO | WO2009104178 A2 | 8/2009 |
| WO | WO2010030363 A1 | 3/2010 |
| WO | WO2010107707 A2 | 9/2010 |
| WO | WO2010/146492 | 12/2010 |
| WO | WO 2010/151875 | 12/2010 |
| WO | WO2014201388 A1 | 12/2014 |
| WO | WO2014201389 A1 | 12/2014 |
| WO | WO2014201719 A1 | 12/2014 |
| WO | WO2015164715 A1 | 10/2015 |

OTHER PUBLICATIONS

"Electrical properties of the epidermal stratum corneum" dated Aug. 12, 1974. By T. Yamamoto and Y. Yamamoto (8 pages).

"Insertion of microneedles into skin: measurement and prediction of insertion force and needle facture force" dated Dec. 10, 2003. By S. P. Davis, B. J. Landis, Z. H. Adams, M. Allen, and M. R. Prausnitz (9 pages).

"Lack of Pain Associated with Microfabricated Microneedles" dated Oct. 10, 2000. By S. Kaushik, A. H. Hord, D. D. Denson, D. V. McAlliser, S. Smitra, M. G. Allen, and M. R. Prausnitz (3 pages).

"Microneedle Insertion Force Reduction Using Vibratory Actuation" dated 2004. By M. Yang and J. D. Zahn (6 pages).

"Non-invasive bioimpedance of intact skin: mathematical modeling and experiments" dated May 2, 2010. By U. Birgersson, E. Birgersson, P. Aberg, I. Nicander, and S. Ollmar (19 pages).

"Optimal Small-Capacitor Biphasic Waveform for External Defibrillation; Influence of Phase-1 Tilt and Phase-2 Voltage." by Yoshio Yamanouchi, et al. , Journal of the American Heart Association, Dec. 1, 1998, vol. 98, pp. 2487-2493 (8 pgs.).

"Polymer Microneedles for Controlled-Release Drug Delivery" dated Dec. 2, 2005. By J-H. Park, M. G. Allen, and M. R. Prausnitz (12 pages).

"Two Dimensional Metallic Microelectrode Arrays for Extracellular Stimulation and Recording of Neurons" dated 1993. By A. B. Frazier, D. P. O'Brien, and M. G. Allen (6 pages).

"Utilizing Characteristic Electrical Properties of the Epidermal Skin Layers to Detect Fake Fingers in Biometric Fingerprint Systems—A Pilot Study" dated Dec. 1, 2004. By O. G. Martinsen, S. Clausen, J. B. Nysaether, and S. Grimnes (4 pages).

\* cited by examiner

BISPHASIC OR MULTIPHASIC PULSE WAVEFORM AND METHOD

PRIORITY CLAIMS/RELATED APPLICATIONS

This application is a continuation of and claims priority under 35 USC 120 to U.S. patent application Ser. No. 15/811,427, filed Nov. 13, 2017 and entitled "Novel Biphasic Or Multiphasic Pulse Waveform Generator And Method" that is a continuation of and claims priority under 35 USC 120 to U.S. patent application Ser. No. 14/662,137, filed on Mar. 18, 2015 and entitled "Novel Biphasic Or Multiphasic Pulse Waveform And Method" that in turn is a continuation in part of and claims priority under 35 USC 120 to U.S. patent application Ser. No. 14/303,541, filed on Jun. 12, 2014 and entitled "Dynamically Adjustable Multiphasic Defibrillator Pulse System And Method" that in turn claims priority under 35 USC 120 and claims the benefit under 35 USC 119(e) to U.S. Provisional Patent Application Ser. No. 61/835,443 filed Jun. 14, 2013 and titled "Dynamically Adjustable Multiphasic Defibrillator Pulse System and Method", the entirety of which is incorporated herein by reference.

FIELD

The disclosure relates to medical devices and in particular to devices and methods that generates and delivers therapeutic electrical treatment pulses used in medical devices, such as cardioverters and defibrillators, neuro-stimulators, musculo-skeletal stimulators, organ stimulators and nerve/peripheral nerve stimulators. More specifically the disclosure relates to the generation and delivery/use by such medical devices of a new and innovatively shaped family/generation of biphasic or multiphasic pulse waveforms.

BACKGROUND

It is well known that a signal having a waveform may have a therapeutic benefit when the signal is applied to a patient. For example, the therapeutic benefit to a patient may be a treatment that is provided to the patient. The therapeutic benefit or therapeutic treatment may include stimulation of a part of the body of the patient or treatment of a sudden cardiac arrest of the patient. Existing systems that apply a signal with a waveform to the patient often generate and apply a well-known signal waveform and do not provide much, or any, adjustability or variability of the signal waveform.

In the context of defibrillators or cardioverters, today's manual defibrillators deliver either an older style Monophasic Pulse (a single high energy single polarity pulse) or the now more common Biphasic Pulse (consisting of an initial positive high energy pulse followed by a smaller inverted negative pulse). Today's implantable cardioverter defibrillators (ICDs), automated external defibrillators (AEDs) and wearable cardioverter defibrillators (WCDs) all deliver Biphasic Pulses with various pulse phase lengths, high initial starting pulse amplitude and various pulse slopes. Each manufacturer of a particular defibrillator, for commercial reasons, has their own unique and slightly different exact timing and shape of the biphasic pulse for their devices' pulses, although they are all based off of the standard biphasic waveform design. Multiple clinical studies over the last couple of decades have indicated that use of these variants of the biphasic waveform has greater therapeutic value than the older monophasic waveform does to a patient requiring defibrillation therapy and that these standard biphasic waveforms are efficacious at appreciably lower levels of energy delivery than the original monophasic waveforms, and with a higher rate of resuscitation success on first shock delivery.

Thus, almost all of the current defibrillator products that use a biphasic waveform pulse have a single high-energy reservoir, which, while simple and convenient, results in severe limitation on the range of viable pulse shapes that can be delivered. Specifically, the second (or Negative) phase of the Biphasic waveform is currently characterized by a lower amplitude starting point than the first (or Positive) phase of the Biphasic waveform, as shown in FIG. 2. This is due to the partial draining of the high-energy reservoir during delivery of the initial Positive phase and then, after inverting the polarity of the waveform so that the Negative phase is able to be delivered, there is only the same partially drained amount of energy remaining in the energy reservoir. This lower amplitude starting point constrains and causes the lower initial amplitude of the Negative phase of the waveform. The typical exponential decay discharge is shown by the Positive phase of the waveform shown in FIG. 2.

The standard biphasic pulse waveform has been in common usage in manual defibrillators and in AEDs since the mid-1990s, and still results in energy levels of anywhere from 120 to 200 joules or more being delivered to the patient in order to be efficacious. This results in a very high level of electrical current passing through the patient for a short period of time which can lead to skin and flesh damage in the form of burns at the site of the electrode pads or paddles in addition to the possibility of damage to organs deeper within the patient's body, including the heart itself. The significant amounts of energy used for each shock and the large number of shocks that these AED devices are designed to be able to deliver over their lifespan, has also limited the ability to further shrink the size of the devices.

WCDs generally need to deliver shocks of 150-200 joules in order to be efficacious, and this creates a lower limit on the size of the electrical components and the batteries required, and hence impacts the overall size of the device and the comfort levels for the patient wearing it.

ICDs, given that they are implanted within the body of patients, have to be able to last for as many years as possible before their batteries are exhausted and they have to be surgically replaced with a new unit. Typically ICDs deliver biphasic shocks of up to a maximum of 30-45 joules, lower than is needed for effective external defibrillation as the devices are in direct contact with the heart tissue of the patient. Subcutaneous ICDs, differ slightly in that they are not in direct contact with the heart of the patient, and these generally deliver biphasic shocks of 65-80 joules in order to be efficacious. Even at these lower energy levels there is significant pain caused to the patient if a shock is delivered in error by the device. Most existing devices are designed to last for between 5-10 years before their batteries are depleted and they need to be replaced.

Another, equally common type of defibrillator is the Automated External Defibrillator (AED). Rather than being implanted, the AED is an external device used by a third party to resuscitate a person who has suffered from sudden cardiac arrest. FIG. 9 illustrates a conventional AED 800, which includes a base unit 802 and two pads 804. Sometimes paddles with handles are used instead of the pads 804. The pads 804 are connected to the base unit 802 using electrical cables 806.

A typical protocol for using the AED 800 is as follows. Initially, the person who has suffered from sudden cardiac arrest is placed on the floor. Clothing is removed to reveal the person's chest 808. The pads 804 are applied to appropriate locations on the chest 808, as illustrated in FIG. 9. The electrical system within the base unit 802 generates a high voltage between the two pads 804, which delivers an electrical shock to the person. Ideally, the shock restores a normal cardiac rhythm. In some cases, multiple shocks are required.

DETAILED DESCRIPTION OF ONE OR MORE EMBODIMENTS

The novel biphasic or multiphasic pulse waveform is applicable for use with various medical devices including all defibrillator types: external (manual, semi-automated and fully automated), wearable and implanted. In addition to defibrillators, the medical device may also be cardioverters and external/internal pacers, as well as other types of electrical stimulation medical devices, such as: neuro-stimulators, musculo-skeletal stimulators, organ stimulators and nerve/peripheral nerve stimulators, whether the devices are external or implantable. The biphasic or multiphasic waveform pulse may be particularly useful for any type of defibrillator and examples of the biphasic or multiphasic waveform pulse will be described in the context of a defibrillator for illustration purposes.

Figure 2:
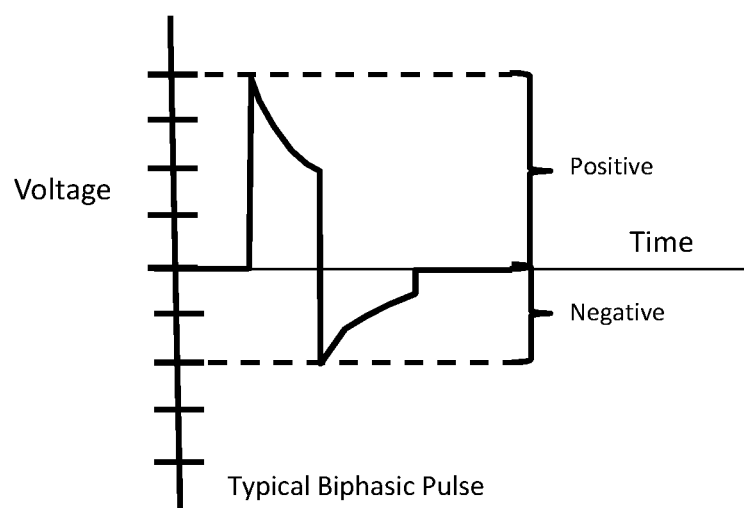
FIG. 2 illustrates a standard biphasic pulse waveform where the second (negative) phase of the waveform is smaller in amplitude than that of the first (positive) phase of the waveform.
Figure 3:
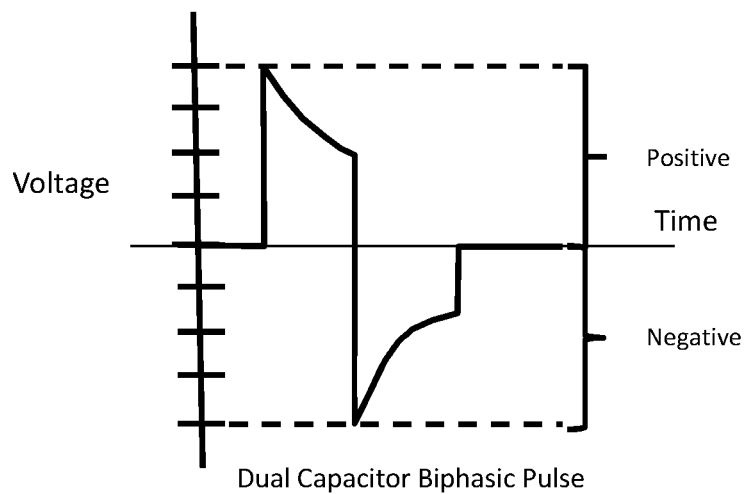
FIG. 3 illustrates the shape of a biphasic waveform where the first phase of the waveform is identical in amplitude to that of the second phase of the waveform.

The novel biphasic or multiphasic waveform pulse is a distinctly different family of waveforms compared to the standard biphasic waveforms (see FIG. 2) which has been used for the past several decades for defibrillators where the second phase's leading edge amplitude is the same as the first phase's trailing edge amplitude. The novel biphasic or multiphasic waveform pulse is also substantially different from the even higher energy dual capacitor biphasic waveform (see FIG. 3) that was explored in the 1980s. The biphasic or multiphasic waveform pulse is a novel family of biphasic, or multiphasic, waveforms where the initial phase of the waveform is smaller in amplitude than the amplitude of the second phase of the waveform (see FIGS. 4A-7 for example). The typical circuitry used to generate the typical biphasic pulse shown in FIG. 2 cannot be used to generate the biphasic or multiphasic waveform pulse described herein.

The novel biphasic or multiphasic waveform pulse allows for an efficacious pulse waveform to be delivered to the patient at a substantially lower level of total energy than ever before. In preclinical animal trials using the novel biphasic or multiphasic waveform pulse, successful defibrillation has been demonstrated using the novel biphasic or multiphasic waveform pulse, repeatedly, and at significantly lower levels of total delivered energy than the energy required by any current external defibrillators using either the original monophasic pulse or the now traditional biphasic pulse. For example, the novel biphasic or multiphasic waveform pulse may deliver 0.1 to 200 joules to a patient. Furthermore, the time for the waveform pulse delivery is between 1-20 ms and preferably 8-10 ms for the combined first and second phases of the waveform, although for triphasic and quadriphasic waveforms this is preferably in the 8-16 ms range for the entire waveform. For an embodiment in which the generated waveform is being used for nerve stimulation or neuro-stimulation, the waveform period may be on the order of microseconds or shorter.

The novel biphasic or multiphasic waveform pulse also significantly reduces both the total energy and the current levels that must be discharged into the patient, thus reducing the chance of either skin burns or other damage to the skin, tissue or organs of the patient. The novel biphasic or multiphasic waveform pulse also reduces the maximum amount of energy that a device is required to store and deliver, and it increases the maximum lifespan of any battery powered device due to a more frugal use of the energy stored within it. The novel biphasic or multiphasic waveform pulse also enables the production of smaller devices as a lower total amount of energy is needed to be stored and delivered to the patient.

Figure 4A:
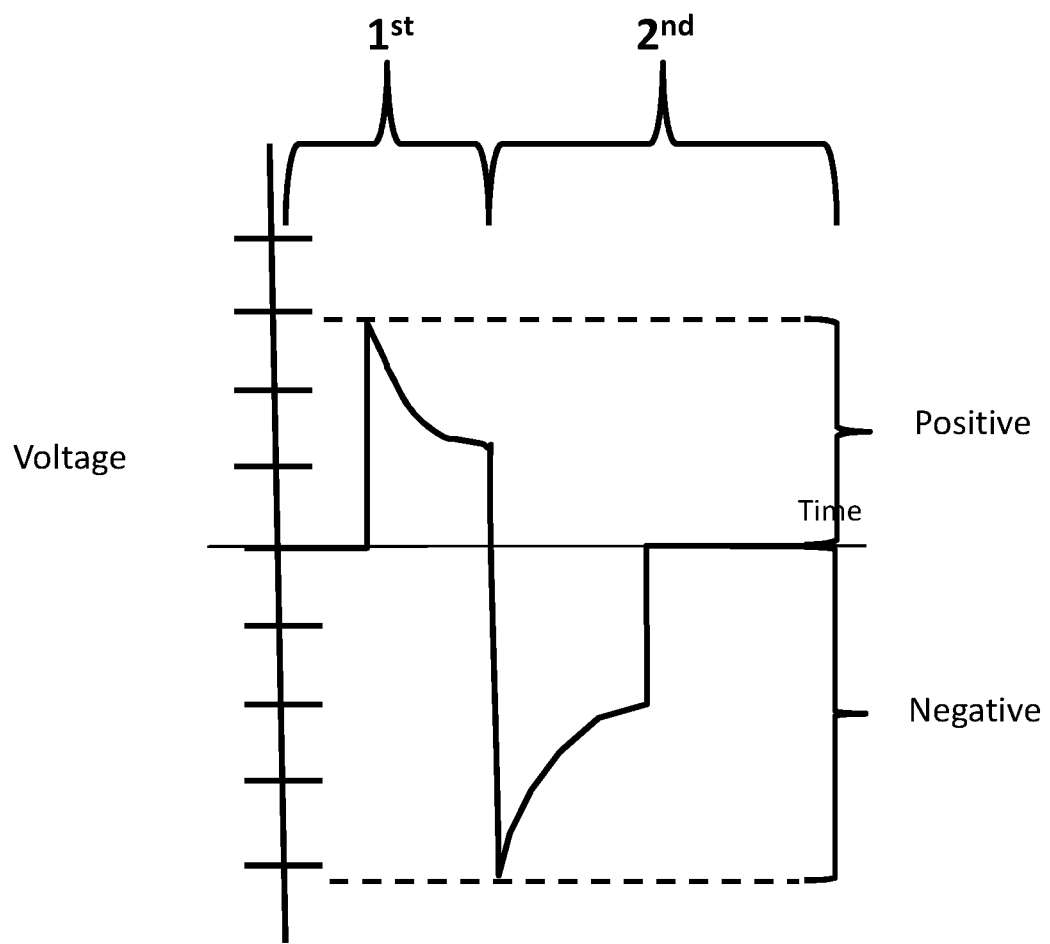
FIGS. 4A and 4B illustrate the shape of a biphasic pulse waveform where the first phase of the waveform is slightly smaller in amplitude than that of the second phase of the waveform.
Figure 4B:
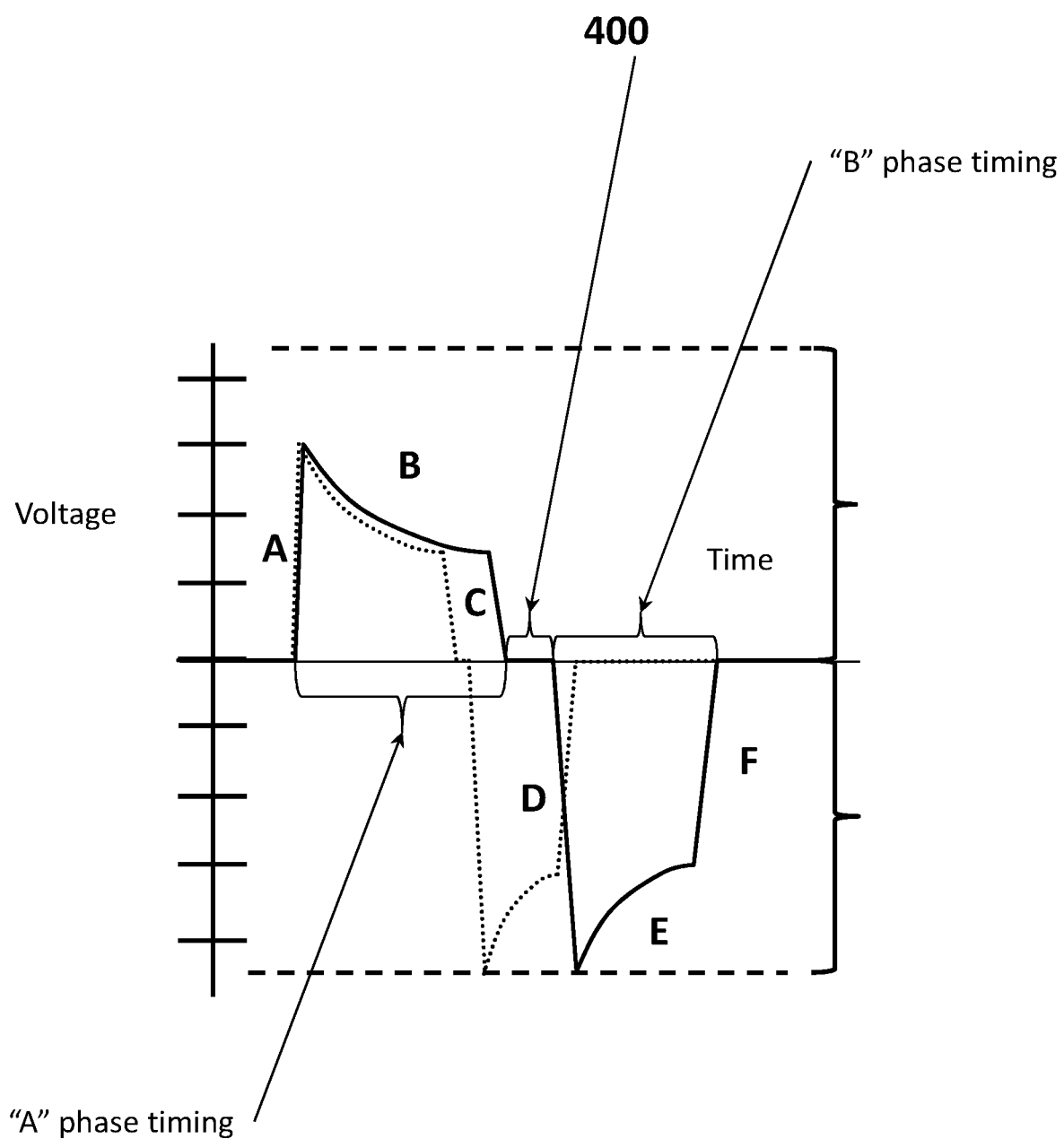

The novel biphasic or multiphasic waveform pulse is effective across a wide range of values for multiple variables/characteristics of the novel biphasic or multiphasic waveform pulse. For example, FIGS. 4A and 4B show a biphasic waveform with a first phase (being positive polarity in this example) and a second phase (being negative polarity in this example) with the amplitude of the first phase being smaller than the second phase. As shown in FIG. 4B, a timing/duration of each phase (phase A and phase B) of the pulse waveform may be at least 1 millisecond for defibrillator medical devices and may be between 1-20 ms and an inter-phase period 400 between the first and second phases may be between 0 to 1500 microseconds. In addition, the first phase (that may be a positive polarity as shown in FIG. 4B or a negative polarity) may have a rise time of the leading edge A and an amplitude of the leading edge A, a time of decay slope B and a phase tilt of the decay slope B, a fall time of trailing edge C and an amplitude of the trailing edge C. In addition, the second phase (that may be a negative polarity as shown in FIG. 4B or a positive polarity, but is an opposite polarity of phase A) may have a rise time of leading edge D, an amplitude of the leading edge D, a time of decay slope E, a phase tilt of the decay slope E, a fall time of trailing edge F and an amplitude of the trailing edge F. The decay slope/tilt, for example, for each phase of the waveform may be between 0% and 95%. Each of the above characteristics of the pulse waveform may be adjusted and optimized depending on the exact therapeutic use to which the waveform is being put, as well as upon the nature and positioning of the device (external or implantable) and also upon the specifics of the patients themselves. Although a biphasic waveform is shown in FIG. 4B, a multiphasic waveform may have multiple phases (each phase with its own duration and amplitude) and multiple inter-phase periods. Each phase of the multiphasic waveform may have independent or the same adjustable rise time, slope time and fall time characteristics.

Figure 5:
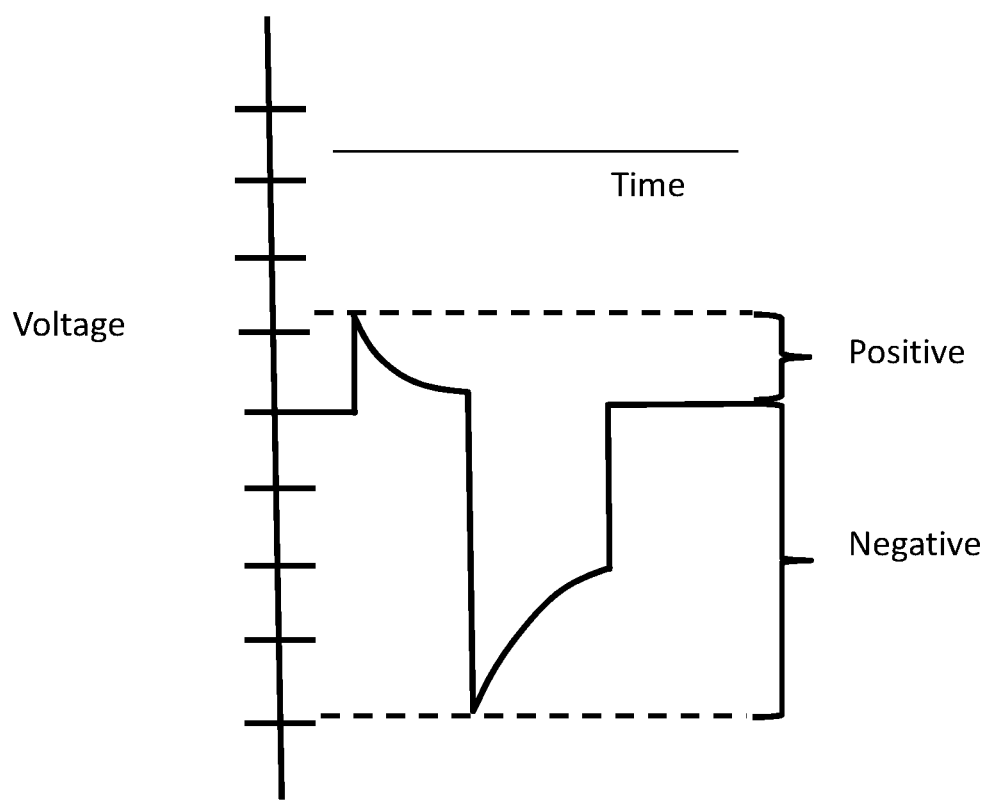
FIG. 5 illustrates the shape of a biphasic pulse waveform where the first phase of the waveform is significantly smaller in amplitude than that of the second phase of the waveform.
Figure 6:
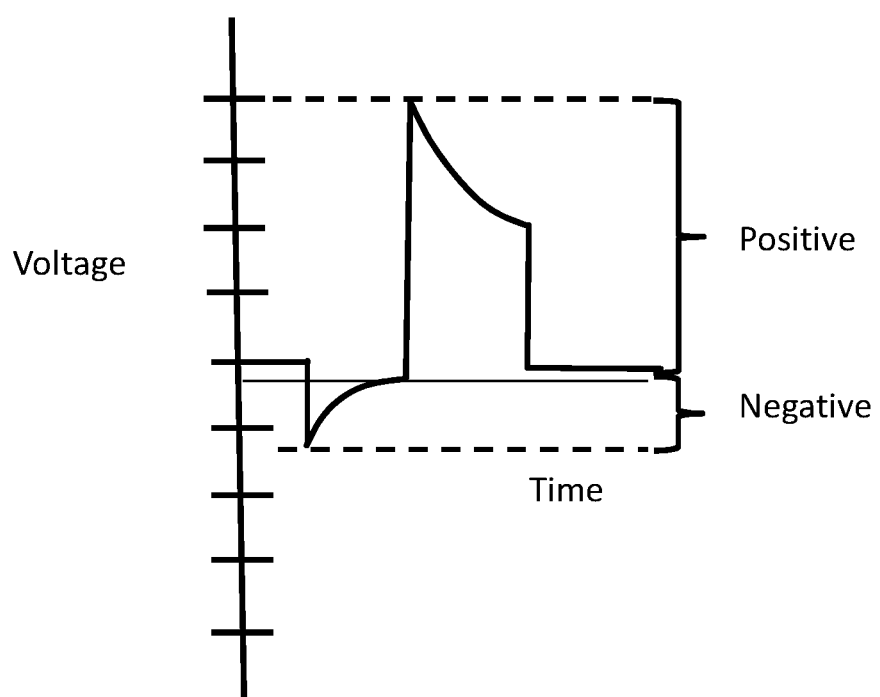
FIG. 6 illustrates the shape of a biphasic pulse waveform where the first phase of the waveform is significantly smaller in amplitude than that of the second phase of the waveform, and where the first phase is a negative phase and the second phase is a positive phase.
Figure 7:
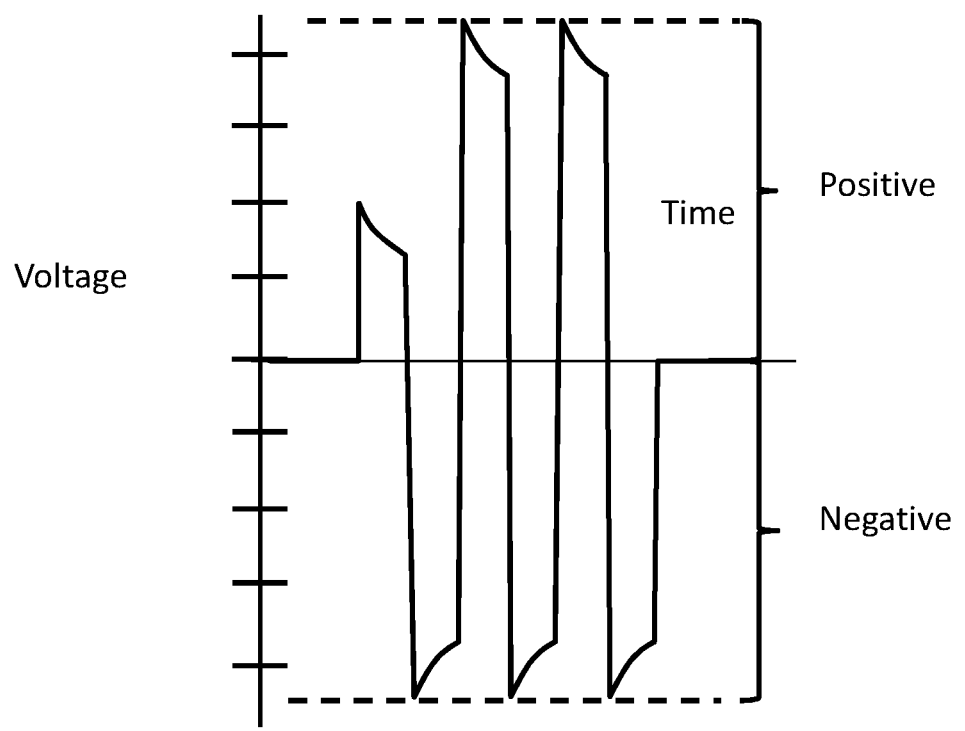
FIG. 7 illustrates the shape of a multiphasic pulse waveform where the initial phase of the waveform is smaller in amplitude than the second phase of the waveform, regardless of the amplitude(s) of any phase(s) subsequent to the second phase of the waveform.
Figure 8:
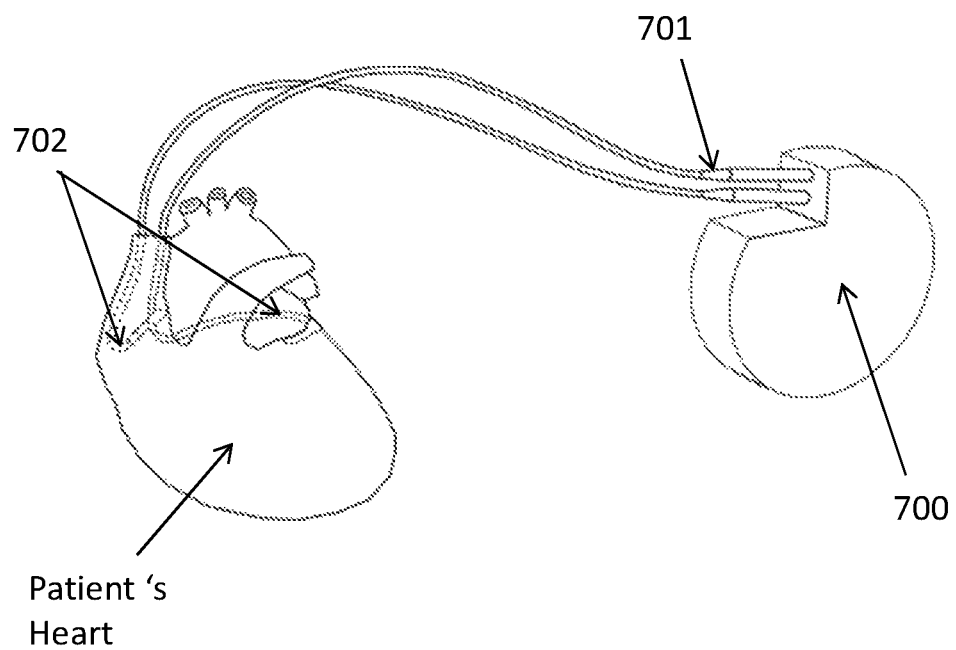
FIG. 8 diagrammatically illustrates an example of a conventional implantable cardioverter defibrillator FIG. 9 diagrammatically illustrates an example of a conventional external defibrillator.
Figure 9:
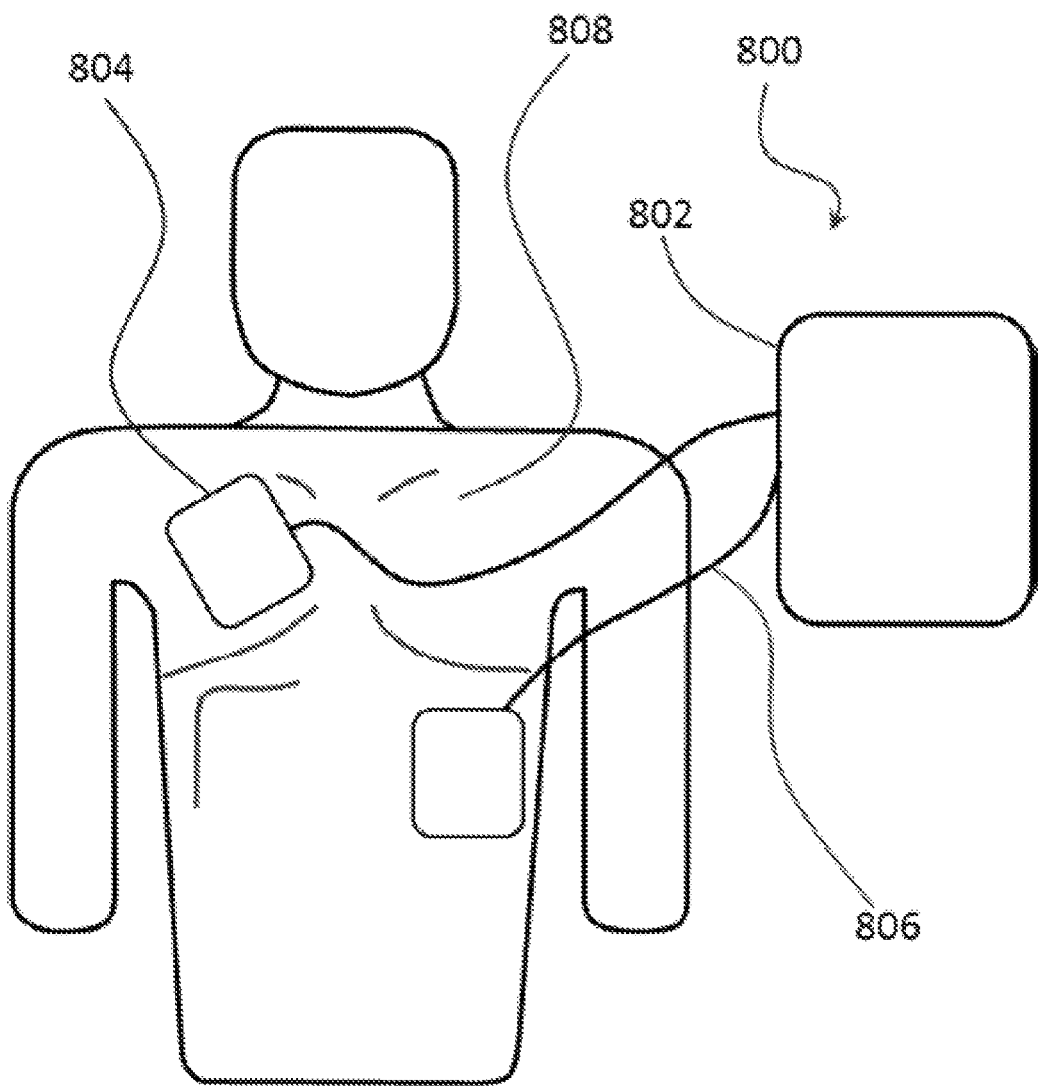

FIGS. 5 and 6 illustrate additional examples of a biphasic waveform. The example in FIG. 5 of the waveform has a first positive polarity phase and a second negative polarity phase. The example in FIG. 6 of the waveform has a first negative polarity phase and a second positive polarity phase. In the biphasic or multiphasic waveforms, the first phase has a polarity and then the second phase has an opposite polarity. FIG. 7 illustrates an example of a multiphasic waveform that has a plurality of positive polarity phases (3 in this example) and a plurality of negative polarity phases (3 in this example). As with the other examples, the amplitude of the first phase is smaller than the amplitudes of the subsequent positive phases and the negative phases.

Figure 10:
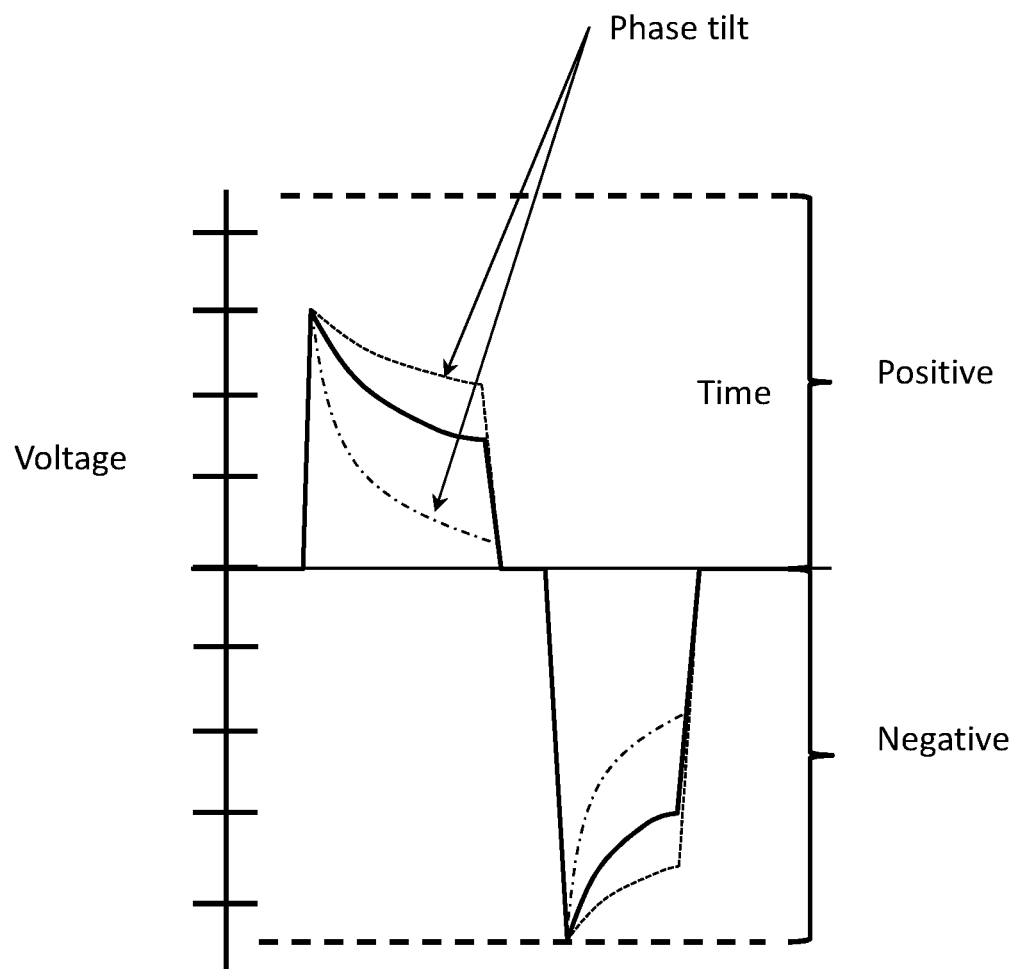
FIG. 10 illustrates a biphasic waveform where the first phase of the waveform is significantly smaller in amplitude than the amplitude of the second phase of the waveform and a range of phase tilt variables for each of the phases are shown diagrammatically.
Figure 11:
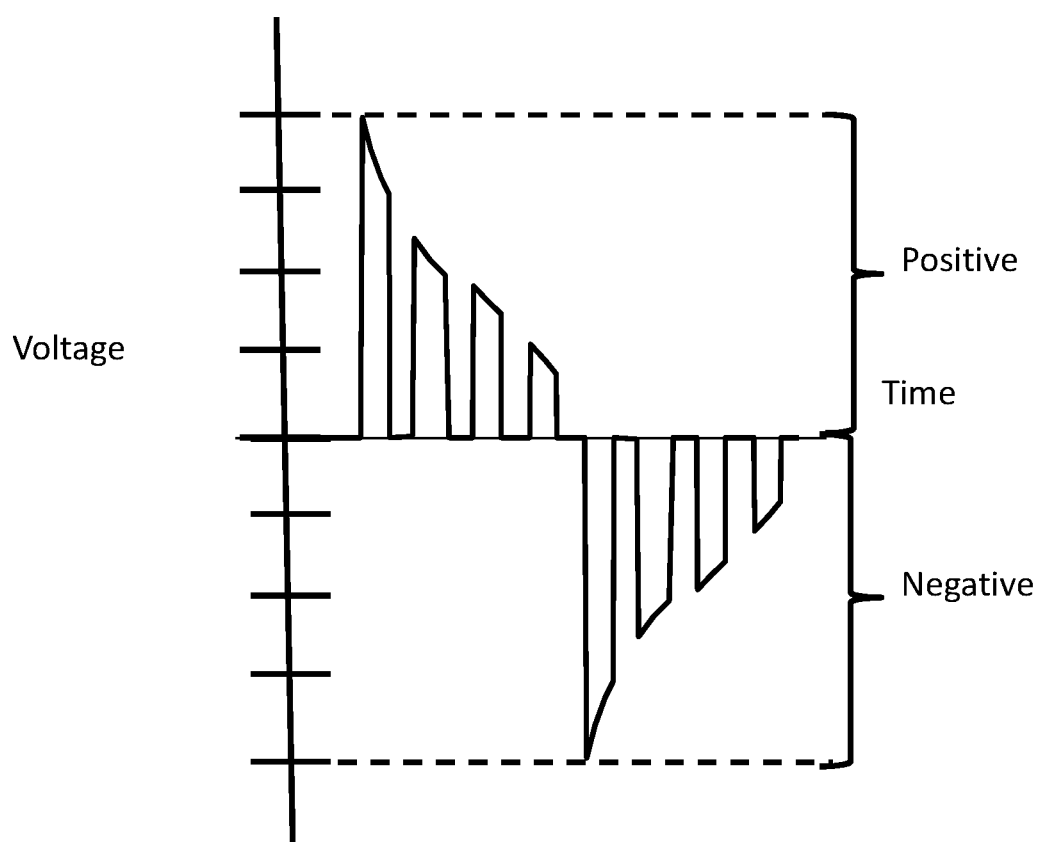
FIG. 11 illustrates a biphasic waveform where each phase of the waveform (equal in size to each other) is switched on and off throughout the delivery process such that only a fraction of the maximum possible energy is actually delivered to the patient.
Figure 12:
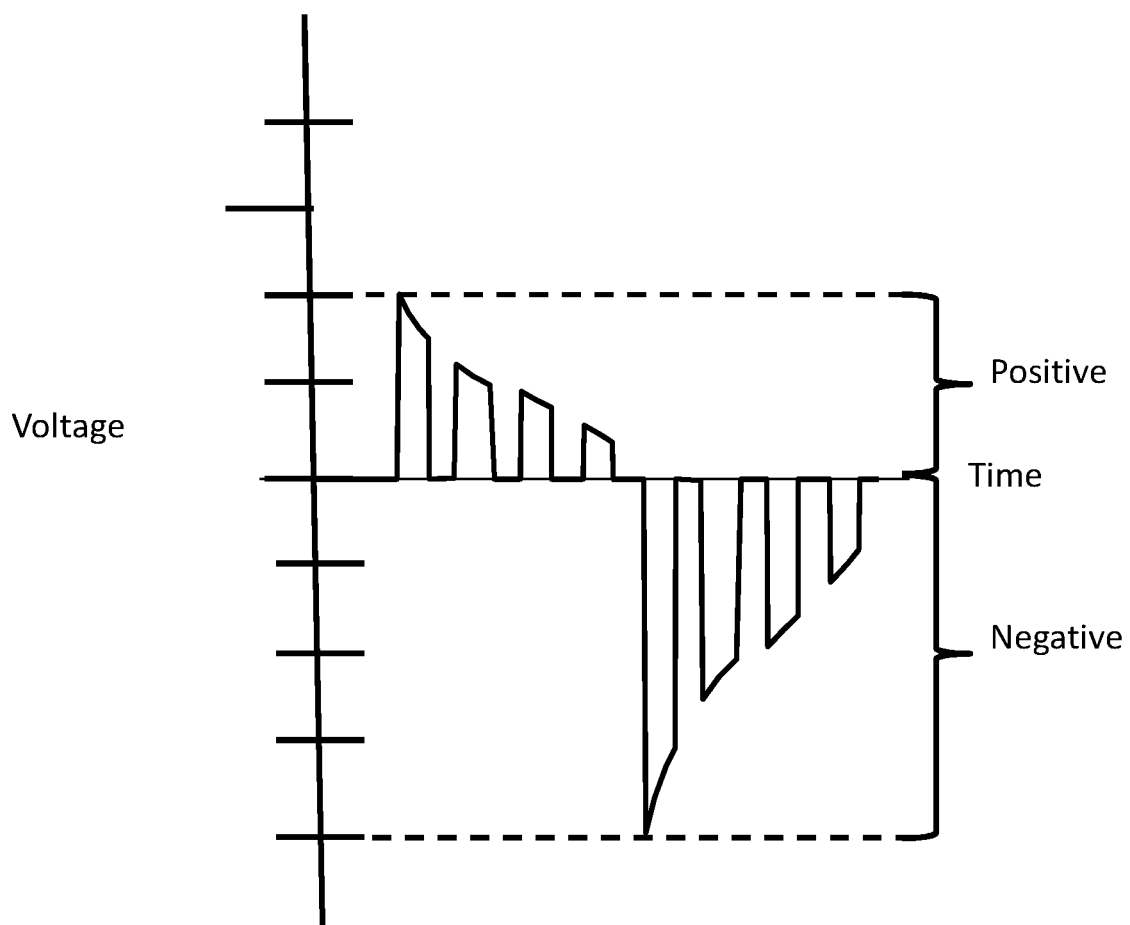
FIG. 12 illustrates a biphasic waveform where each phase of the waveform, where the first phase is smaller in amplitude than the second phase, is switched on and off throughout the delivery process such that only a fraction of the maximum possible energy is actually delivered to the patient.

In an additional embodiment, the novel biphasic or multiphasic waveform pulse may have different phase tilts for either or both phases as shown in FIG. 10. In addition, the novel biphasic or multiphasic waveform pulse may be generated and delivered to the patient in a lower energy manner, by only delivering portions of the pulse waveform to the patient. This can be done with the whole waveform (see FIG. 11 and FIG. 12) or else with individual phases of the waveform according to the energy conservation needs and the therapeutic needs. This can be accomplished via multiple means, including internal and external shunting of the current using high speed switching. In FIGS. 11-12, the novel biphasic or multiphasic waveform pulse may have a plurality of first phase pulses (with the same polarity) and then a plurality of second phase pulses that each have the same polarity, but opposite of the polarity of the first phase.

Figure 1:
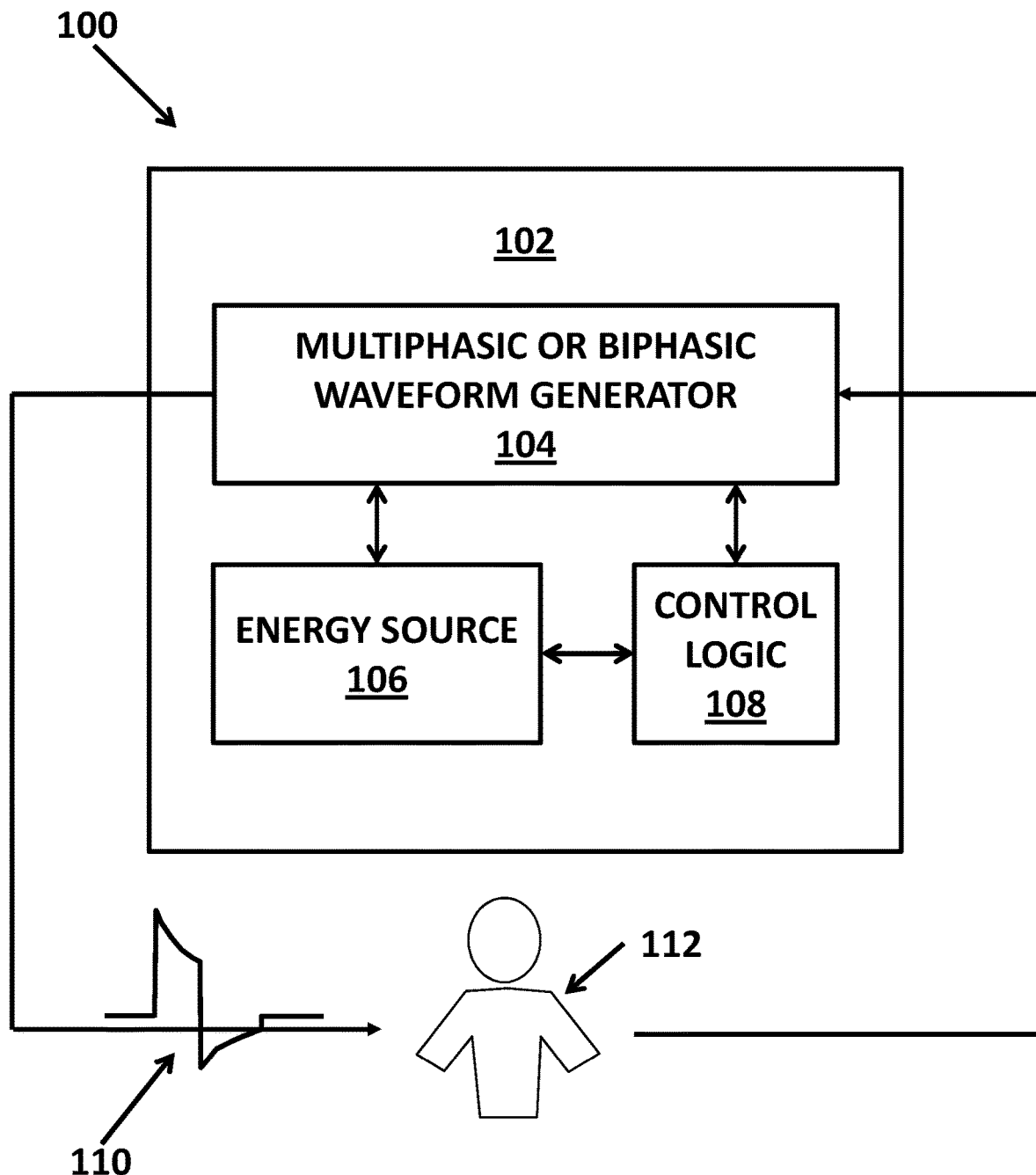
FIG. 1 illustrates a medical device that may generate and deliver a biphasic or multiphasic waveform.

The novel biphasic or multiphasic waveform pulse may be generated in various manners. For example, as shown in FIG. 1, a medical device 102 may have a biphasic or multiphasic waveform generator 104 and an energy source 106 that may be coupled to a control logic unit 108. The control logic unit may control the biphasic or multiphasic waveform generator 104 and the energy source 106 to generate the biphasic or multiphasic waveform pulse. One skilled in the art would understand that various circuitry for the biphasic or multiphasic waveform generator 104, the energy source 106 and the control logic unit 108 may be used to generate the biphasic or multiphasic waveform pulse. An example of circuitry that may be used to generate the biphasic or multiphasic waveform pulse may be found in co-pending U.S. patent application Ser. No. 14/661,949, filed on Mar. 18, 2015, that is incorporated herein by reference.

While the foregoing has been with reference to a particular embodiment of the disclosure, it will be appreciated by those skilled in the art that changes in this embodiment may be made without departing from the principles and spirit of the disclosure, the scope of which is defined by the appended claims.

The invention claimed is:

1. An apparatus, comprising:
a generator that generates a therapeutic defibrillation waveform having at least one first phase having a first polarity and a duration of 1-20 milliseconds, an inter-phase period immediately following the at least one first phase and at least one second phase immediately following the inter-phase period having a polarity opposite of the first polarity and a duration of 1-20 milliseconds wherein an amplitude of a leading edge of the at least one first phase is less than an amplitude of a leading edge of the at least one second phase; and
wherein the at least one first phase has a set of characteristics including a rise time of the leading edge, a decay slope from the leading edge to a trailing edge having a time period of the decay slope and a phase tilt of the decay slope between zero percent and ninety-five percent and the therapeutic defibrillation waveform is adjusted based on the phase tilt of the at least one first phase and the at least one second phase has a set of characteristics including a rise time of the leading edge, a decay slope from the leading edge to a trailing edge having a time period of the decay slope and a phase tilt of the decay slope between zero percent and ninety-five percent and the therapeutic defibrillation waveform is adjusted based on the phase tilt of the at least one second phase, wherein each characteristic of the set of characteristics of the at least one first phase and the at least one second are adjustable.

2. The apparatus of claim 1, wherein the inter-phase period between the at least one first phase and the at least one second phase is adjustable between 0 and 1500 microseconds.

3. A method, comprising:
generating, by a generator, a therapeutic defibrillation waveform having at least one first phase having a first polarity and a duration of 1-20 milliseconds, an inter-phase period immediately following the at least one first phase and at least one second phase immediately following the inter-phase period having a polarity opposite of the first polarity wherein an amplitude of a leading edge of the at least one first phase is less than an amplitude of a leading edge of the at least one second phase, wherein the at least one first phase has a rise time of the leading edge, a decay slope from the leading edge to a trailing edge having a time period of the decay slope and a phase tilt of the decay slope; and
optimizing the therapeutic defibrillation waveform by adjusting each of the phase tilt of the decay slope of the at least one first phase and at least one second phase between zero percent and ninety-five percent.

4. The method of claim 3, wherein the at least one second phase further comprises a rise time of the leading edge, a decay slope from the leading edge to a trailing edge having a time period of the decay slope and a phase tilt of the decay slope, and wherein optimizing the therapeutic defibrillation waveform further comprises adjusting the phase tilt of the decay slope of the at least one second phase between zero percent and ninety-five percent.

5. The method of claim 4, wherein the inter-phase period between the at least one first phase and the at least one second phase is adjustable between 0 and 1500 microseconds.

\* \* \* \* \*